United States Patent
Adamy et al.

(10) Patent No.: US 6,973,894 B1
(45) Date of Patent: *Dec. 13, 2005

(54) TIMING DEVICE

(75) Inventors: Steven T. Adamy, Princeton, NJ (US); Francis R. Cala, Highland Park, NJ (US)

(73) Assignee: Church & Dwight Co., Inc., Princeton, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 10/416,066

(22) PCT Filed: Nov. 8, 2000

(86) PCT No.: PCT/US00/30697

§ 371 (c)(1),
(2), (4) Date: May 7, 2003

(87) PCT Pub. No.: WO02/39196

PCT Pub. Date: May 16, 2002

(51) Int. Cl.⁷ ............................................. G01N 31/22
(52) U.S. Cl. .................. 116/206; 116/200; 368/327; 422/61; 436/164
(58) Field of Search .............. 116/206–207, 200, 116/216, 219; 368/327; 426/87–88; 374/102–108; 422/58, 61, 82.05; 436/164, 166, 169

(56) References Cited

U.S. PATENT DOCUMENTS

| | | | |
|---|---|---|---|
| 244,105 A | * 7/1881 | Bahmann ..................... 374/105 |
| 2,560,537 A | 7/1951 | Anderson |
| 2,671,628 A | 3/1954 | Clark |
| 3,242,733 A | 3/1966 | Johnson |
| 3,414,415 A | 12/1968 | Broad, Jr. |
| 3,479,877 A | 11/1969 | Allen et al. |
| 3,751,382 A | 8/1973 | Ljungberg et al. |
| 3,768,976 A | 10/1973 | Hu et al. |
| 3,942,467 A | 3/1976 | Witonsky |
| 3,951,098 A | 4/1976 | Meyers |
| 3,954,011 A | * 5/1976 | Manske ..................... 374/102 |
| 3,996,007 A | 12/1976 | Fang et al. |
| 4,028,876 A | 6/1977 | Delatorre |
| 4,408,557 A | 10/1983 | Bradley et al. |
| 5,114,679 A | * 5/1992 | Reifler et al. ............... 422/100 |
| 5,602,804 A | 2/1997 | Haas |
| 6,269,764 B1 | * 8/2001 | Adamy et al. .............. 116/206 |
| 2004/0013048 A1 | * 1/2004 | Adamy ..................... 368/327 |

* cited by examiner

Primary Examiner—G. Bradley Bennett
Assistant Examiner—Tania C. Courson
(74) Attorney, Agent, or Firm—Stephen B. Shear; Allen R. Kipnes

(57) ABSTRACT

A timing device for visually determining the passage of a preselected period of time including a tube (2) having opposed ends with at least one of the opposed ends having a reservoir (10a, 10b) for storing a reactant or an indicator, a transport system (12) extending from the reservoir to the other of the opposed ends of the tube (2) for transporting at least one of the reactant or the indicator until they contact each other, a reactant, and an indicator which when in contact with the reactant via the transport means (12) emits an observable change in property wherein the minimum length of the period of time corresponds to the time it takes for the reactant and indicator to contact each other. The tube (2) has a shape which undergoes at least two material changes of direction exceeding 90° and up to 180° from one of the opposed ends to the other.

44 Claims, 5 Drawing Sheets

TIMING DEVICE

RELATED APPLICATION

This application is related to U.S. patent application Ser. No. 09/311,949 filed on May 14, 1999.

FIELD OF THE INVENTION

The present invention is generally directed to a timing device for visually determining the passage of a preselected period of time which is applicable to a wide variety of consumer products, especially for products which have an extended shelf or use life and for which it is desirable to know when the product must be replaced or rejuvenated. The timing device can be attached to or incorporated in typical packaging employed for consumer products.

BACKGROUND OF THE INVENTION

Consumer products including food products, cleaning products, deodorizers and the like have a shelf life determined by the length of time the components of the product resist change to environmental influences. For example, food products have a given shelf life based on their ability to resist chemical or physical changes due to contact with air, heat and other influences in the environment. Many consumer products are date stamped to provide the user with an indication of the shelf life of the product. The shelf life may be relatively short such as a few days or may be relatively lengthy such as a few months. Date stamping of consumer products provides the user with some indication when the product may no longer be useful for its intended purpose.

Quite often, date stamps are printed Inconspicuously on the product package. It is sometimes difficult to read the date stamp and in some cases even to find the date stamp because it may be printed anywhere on the package. Date stamping is particularly problematic for products which have a relatively long shelf life because such products tend to get stored in an obscure recesses of a storage area, such as a food cabinet or refrigerator. If the product is not used often, the consumer is often unaware that the expiration date is shortly forthcoming or has even passed.

There have been attempts to provide a visible indication of when the useful life of a product has expired. So called "life time indicators" are employed for food products such as disclosed in U.S. Pat. Nos. 2,671,028; 3,751,382; and 3,942,467. These indicators typically work through chemical reactions initiated or increased in rate by exposure to high temperatures. Other lifetime indicators rely on diffusion of a component through a traditional wick or membrane as disclosed in U.S. Pat. Nos. 3,414,415; 3,479,877 and 3,768,976, each of which is incorporated herein by reference.

Examples of such products include, for example, the Oral-B toothbrush indicator which is based on the diffusion of a dye out of the bristles. When the color of a select group of bristles disappears, the user is aware that the toothbrush may or should be discarded and replaced. Another example is the Glade Neutralizer which is a deodorizer product having a timer based on the evaporation of a solvent from a polymer gel and subsequent shrinkage of the gel.

The timing indicators mentioned above suffer from one or more disadvantages which makes their universal applicability to a wide range of packaged products problematical. Such disadvantages include a) the timing mechanism is part of the product (e.g. a deodorizer) and is therefore limited to employment with that product or that class of products, b) the timing mechanism is inaccurate or cannot be controlled to accommodate a wide range of product shelf lives, c) the timing mechanism is expensive and/or d) has a limited range of measurement.

To overcome these problems, Applicants developed a shelf life indicator or timing device which comprised an inverted U-shaped tube having opposed ends with at least one of the opposed ends having a reservoir for storing a reactant or an indicator and a transport means extending from the reservoir to the other of the opposed ends of the tube for transporting at least one-of the reactant or the indicator until they contact each other. When the reactant and indicator are in contact with each other there is an observable change of property, such as a color change which may be used as a measure of the passage of certain period of time. Such timing devices are disclosed in related U.S. patent application Ser. No. 09/311,949 filed May 14, 1999, incorporated herein by reference.

It has been observed that when such timing devices are reduced in scale to accommodate relatively small packages, the measurable period of time is reduced. In some cases the reduction in the measurable period of time may be reduced to a greater extent than the reduction in scale of the timing device.

It would therefore be an advance in the art of providing visible indicators for determining when a product should be replaced or rejuvenated if a cost efficient and effective shelf life indicator could be provided which provides a clear and distinct visible indication of when a product should be replaced or rejuvenated. It would be a further advance in the art if a shelf life indicator could be provided which enables the consumer to see how much time is remaining for the shelf life of the product which indication is accurate and clearly visible. It would be a still further advance in the art if a shelf life indicator could be provided which maintained a useful measurable period of time even when reduced in scale to accommodate relatively small packages.

SUMMARY OF THE INVENTION

The present invention is generally directed to a shelf life indicator hereinafter referred to as a "timing device" for determining the remaining shelf life of a product and visually displaying the same which has applicability to a wide range of consumer products and packages containing the same. The timing device can be applied to products which have a relatively short shelf life (e.g. dairy products including milk) and products which have a fairly long shelf life such as canned vegetables.

In a particular aspect of the present invention, there is provided a timing device for determining and visually displaying the passage of a preselected period of time comprising:

a) a tube having opposed ends with one of the opposed ends extending downwardly below the level of the remaining portion of the tube, one of said opposed ends having a reservoir for storing a reactant or an indicator, said tube undergoing at least two material changes in direction from one of the opposed ends to the other, b) transport means extending from the reservoir to the other of the opposed ends of the tube for transporting at least one of the reactant or the indicator until they contact each other, c) a reactant: and d) an indicator which when in contact with the reactant via the transport means emits an observable change in a property wherein the minimal length of the period of time corresponds to the time it takes for the reactant and indicator to contact each other.

Methods of employing the device, packages employing the device and methods of manufacturing the device also constitute a part of the invention set forth herein.

BRIEF DESCRIPTION OF THE DRAWINGS

The following drawings in which like reference characters indicate like parts are illustrative of embodiments of the invention and are not intended to limit the invention as encompassed by the claims forming part of the application.

DETAILED DESCRIPTION OF THE INVENTION

Figure 1:
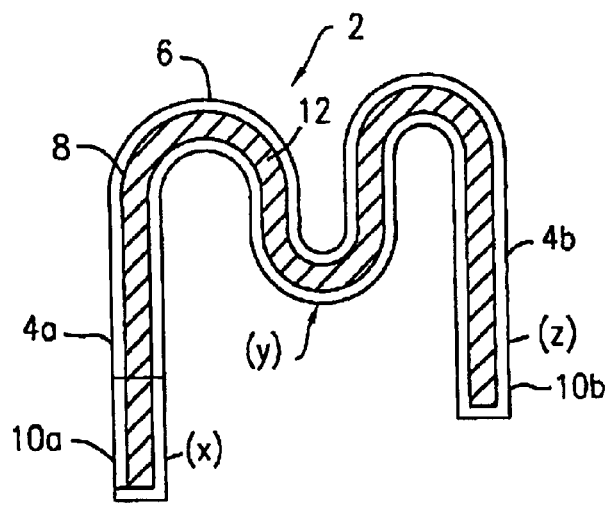
FIG. 1 is a front elevational view of a first embodiment of the timing device of the present invention.

The present invention is generally directed to a timing device for visually determining the passage of a preselected measurable period of time in which the timing device has particular applicability to visually indicating the remaining shelf life of a product, especially consumer products such as food products and household products. The main component of the timing device is a tube which contains two components, a reactant and an indicator as more fully described hereinafter. The shape of the tube is particularly adapted to accommodate a desirable measurable period of time on relatively small packages although such devices may be readily applied to all sized packages including large packages as well. Contact of the reactant and indicator directly or indirectly produces a visible change in at least one property, preferably a color change which can indicate that the product should be replaced or rejuvenated, the amount of time which has passed since the product was used, and/or the amount of time remaining before the product must be replaced or rejuvenated. Of particular importance to the present invention is the pathway provided by the tube enabling the reactant and indicator to come into contact with each other. Control over the shape of the tube enables control over the period of time it takes for the reactant and indicator to come into contact and where in the timing device they come into contact which provides the timing device with the means by which the above-mentioned measurable periods of time can be realized.

It has been observed from timing devices employing an inverted U-shaped tube disclosed in Applicants' related U.S. Ser. No. 09/311,949 filed May 14, 1999 that a reduction of scale to accommodate relatively small packages may result in an even larger reduction in the period of time which may be measured with the smaller scale timing device. By way of example, a timing device of the type disclosed in said copending application having a height of about 9 cm and a tube diameter of about 0.6 cm was able to provide a measurable period of time of about 52 days. When the same timing device using the same structural components, reactant and indicator was reduced in scale by about 30% there resulted about a 70% reduction in the measurable period of time. A further reduction in scale of about 30% resulted in about a 40% further reduction in the measurable period of time.

The present invention was developed to at least reduce the significant decrease in the measurable period of time as a result of reducing the scale of the timing device to accommodate relatively small packages. To this end, Applicants determined that by increasing the number of "material changes of direction" as hereinafter defined of the flowing indicator or reactant as compared to the inverted U-shaped tube, the speed of flow may be reduced and the reduction in the length of the measurable period of time is eliminated or at least minimized. As used herein the term "material change of direction" shall mean a change of the flow direction of the indicator or reactant in the tube of greater than 90° and up to 180°. The number of material changes of direction can be computed by determining the number of times that tube undergoes a change of direction greater than 90° and up to 180° before commencing another change in direction.

A first embodiment of the timing device of the present invention is shown in FIG. 1. The tube generally defines a pathway having at least two-material changes of direction (i.e. at least two changes of direction of at least 90° up to 180°) which enables a slower flow of the reactant or indicator as compared with an inverted U-shaped tube. The tube 2 is comprised of a pair of spaced apart and parallel leg portions 4a and 4b connected to each other through a curvilinear central portion 6 providing at least three material changes in direction for the flow of the fluid contained therein as hereinafter explained. The opposed leg portions 4a and 4b and the central portion 6 thereby define a continuous passageway 8.

Each of the leg portions 4a and 4b have a corresponding reservoir 10a and 10b at the respective ends of the leg portions 4a and 4b. At least one of the reservoirs will contain a reactant and the other of the reservoirs may contain an indicator as explained in more detail hereinafter. As shown in FIG. 1, one of the leg portions (e.g. leg portion 4a) extends further downward than the other leg portion (e.g. leg portion 4b).

In one embodiment of the invention, the reactant is contained within one of the reservoirs and the indicator is contained within the other of the reservoirs 10a and 10b. In accordance with the present invention, there is provided a means for transporting at least one of the reactant and the indicator so that they may contact each other and thereby cause a visible change in property (e.g. a color change) which is an indication of the passage of time corresponding to all or a portion of the shelf life of a product.

The preferred transportation means represented by 12 in FIG. 1 is a porous material, most preferably a wicking material which can absorb the reactant and/or the indicator and allow the reactant and/or indicator to pass therethrough.

The preferred wicking materials are those selected from the group consisting of woven fabrics, non-woven fabrics and combinations thereof. What is particularly important for the wicking material is to enable the reactant and/or indicator to move therethrough and travel at least a portion of the distance from one reservoir to another. The distance of travel must be sufficient to enable the reactant and indicator to contact each other and thereby react producing a visible change in a property such as a color change.

The time it takes for a liquid to pass through a wicking material is dependent on how well the liquid wets the material. The employment of polar liquids and wicking materials of lower polarity generally result in longer wicking times. Polar liquids and polar wicking materials generally result in a timing device where the passage of the liquid is more rapid (i.e. shorter wicking times).

Specifically preferred wicking materials include polyesters, polyacrylates, polyacrylamides, polypropylene, polyethylene terephthalate and copolymers thereof, cellulosic materials (including but not limited to natural or synthetic cotton, wood, paper and cellulosic polymers), wool, fiberglass, silica gel, ceramics and combinations thereof.

Low polarity wicking materials include polypropylene and polyethylene terephthalate. Relatively high polarity wicking materials include paper, cotton, wool and silica gel. The polarity of the wicking material can be altered and hence the time of travel of the liquid therethrough by producing blends of low and high polarity wicking materials. An example of such a blend is the combination of polyethylene terephthalate and cotton which are typically made by cross linking the hydroxyl groups of the cotton with reactive functional groups of the polyethylene terephthalate.

The density of the wicking material may be a factor in controlling the rate of absorption of the reactant and/or indicator. Generally, the denser the wicking material, the slower the rate of adsorption. By selecting a suitable wicking material and density thereof, one is able to control the rate at which the reactant and/or indicator proceeds through the wicking material to enable the reactant and indicator to come into contact with each other and thereby cause a visible change in properties.

The physical structure of the wicking material also can influence the rate at which a fluid passes through the timing device. For example, fluid flow can be affected by the type of weave and whether the wicking material has a uniform profile (e.g. having a uniform circular cross-section) or has a non-uniform profile such as a corrugated structure or combinations thereof.

The tube 2 as shown in FIG. 1 can be fabricated from any number of materials including plastics and glass. It is preferred that the material used to construct the tube 2 be unbreakable to prevent injury to the consumer. Preferred materials are plastics including, for example, polyethylene and polyethylene terephthalate.

The tube 2 must enable the user to observe a color change or other change of property that occurs within the tube. Thus, the term "clear" as used herein means that the tube can be transparent or translucent, but not opaque. The tube 2 itself may be colored so long as the color change taking place within the tube can be observed by the user.

The reactant and indicator may be selected from solids, liquids or gases so long as the reactant and indicator are able to contact each other. Liquid reactants and indicators are preferred because gaseous reactants and indicators tend to travel over a relatively short period of time because they more readily diffuse through the tube 2 and are more difficult to control using the wicking material present therein. Where desirable, one, but not both of the indicator and reactant may be a solid.

The reactant and indicator are selected so that when in contact with each other there is a visible change of properties such as a color change. The reactant can be selected from acids, bases, oxidizing agents and reducing agents. The indicators are those materials which when in contact with the reactant cause the change in properties which are visible to the user. For example, indicators include litmus compounds, methyl orange, bromocresol green and congo red.

The change in property which results in a change observable by the user may be from the direct interaction of the indicator and reactant or through an intermediary substance. Direct interaction indicators are those which change color through direct contact with the reactant. Examples of direct indicators are so-called redox indicators such as thymolindolphenol and neutral red. Thymolindolphenol is colorless in its reduced form. Upon contact with a suitable oxidizing agent (e.g. $Fe^{+3}$), thymolindolphenol is oxidized and thereby turns blue.

Neutral red is likewise colorless in reduced form. When oxidized in the presence of a suitable oxidizing agent, neutral red turns red. Other redox reactions may be employed to effect a visible color change including the conversion of $CrO_2^-$ (green) to $CrO_4^{-2}$ (yellow).

The above-mentioned redox systems are examples of direct interaction systems. Such systems produce a change of property by direct reaction of the reactant and indicator.

In some reactant-indicator systems, it is possible to extend the time before the reactant and indicator react to produce a change of property by employing a scavenger for one of them. For example, a reactant ($Fe^{-3}$), scavenger ($Cu^{+1}$) and indicator (e.g. thymolindolphenol) are contained within the timing device. Before the indicator can undergo a color change, the reactant first reacts with the scavenger. Alternatively, another method of obtaining a further delay is to initiate a series of reactions such that a first reactant and a co-reactant produce a first intermediate. The first intermediate can either react with the indicator or with a second co-reactant to produce second intermediate which second intermediate reacts with the indicator to produce a color change. Any number of intermediary reactions and intermediates may be employed as desired.

Other reactant-indicator pairs and scavengers used therewith are known and available such as the employment of a system including $Ti^{+2}$ (indicator), $Fe^{+3}$ (scavenger) and neutral red (indicator).

In another reactant-indicator system, the reactant may be water which induces a color change from a reactant which is an anhydrous compound. For example, cobalt chloride is an anhydrous compound which is blue. Upon contact with water (reactant), the cobalt chloride converts to the hydrated form which has a pink color. Other anhydrous compounds which are suitable for use in the present invention would be known to those of ordinary skill in the art.

In the embodiment shown specifically in FIG. 1, there is employed two reservoirs 10a and 10b. The reactant may be contained in the reservoir 10a and the indicator may be contained in the reservoir 10b. The wicking material 12 is contained within the passageway 8 extending from the reservoir 10a to the reservoir 10b. The selection of a suitable wicking material will enable at least one of the reactant and indicator to travel up the wicking material until the reactant contacts the indicator. If both the reactant and indicator travel through the wicking material, they will meet at some location in the wicking material depending on the relative rates of absorption of the reactant and indicator. Thus, the visible color change will take place at some point along the wicking material and the time it takes for that visible color change to take place is the period of time coinciding with the desirable shelf life of the product. If desired, a portion of the tube may be opaque or hidden so that a visible window area is present at a different location than where the reactant and indicator initially react. If the indicator is not absorbed by the wicking material then the color change will take place in the reservoir 10*b* after the reactant has traveled the full distance through the wicking material from the reservoir 10*a* and to the reservoir 10*b*.

For longer periods of time, the reactant (which can be a solvent) may be a liquid or in solution and the indicator may be solid. The tube is opaque except for a window. The liquid traverses the tube to reach the solid indicator, dissolves the Indicator, and draws the dissolved indicator back along the wicking material until the window portion of the tube is reached and a visual observation can be made.

The employment of a reactant and indicator pair provides a fixed period of time before a color change takes place depending on the type and density of the wicking material. Quite often, it is desirable to modify the rate at which the reactant and/or the indicator travel through the wicking material in order to provide a longer or shorter shelf life measurement which may be accomplished by adding a viscosity modifying agent. The employment of a viscosity modifying agent is dependent in part on the recognition that when the reactants and/or indicators are liquids they typically move through the wicking material in opposite directions which will impede the forward progress of each flow. Furthermore, the viscosity of the reactant and/or indicator will have an effect on the rate of movement of the same through the wicking material. As previously indicated if a modification of the rate of movement is desired a viscosity modifying agent may be used.

In accordance with the present invention, a viscosity modifying agent may be added either to the reactant or to the indicator or to both. The viscosity modifying agent, depending on its viscosity, can be used to speed up or slow down the rate of travel of the reactant and/or indicator. The slowing down of the travel time is desirable when the shelf life of the product is relatively long. The speeding up of the travel time is desirable for those products having a relatively short shelf life.

Viscosity modifying agents for use in the present invention are desirably compatible with the other components (i.e. reactants and indicators) in that they do not cause any change in the composition of the components or the manner in which they react with each other. Another desirable property of the viscosity modifying agents is that they are able to be absorbed and passed through the wicking material without adversely affecting the reactant and indicator. Still further, it is desirable that the viscosity modifying agent be nontoxic, particularly when associated with products used by consumers. Typical examples of viscosity modifying agents for use in the present invention include water, glycerine, alkylene glycols (e.g. propylene glycol) and combinations thereof.

The amount of the reactant, indicator, and optional viscosity modifying agent will vary. The amounts selected for each of the components are made to ensure a visible change in property after a desirable preselected period of time (i.e. the length of the time of the shelf life of the product). The amount of each of these components should be sufficient to travel through the wicking material for the estimated distance of travel to have contact of the reactant and indicator. This represents a minimum amount of the components to achieve the desired time period measurement more than the minimum amount of each component can be used to ensure a proper reaction at a desirable location within the timing device. Generally, the amount of the reactant is at least 0.01% by weight and most typically from about 0.01 to 5.0% by weight, based on the total weight of the materials of the reactant solution. The amount of the indicator is typically at least 0.01% by weight, most typically within the range of from about 0.01 to 0.5% by weight and the amount of the viscosity modifying agent, if necessary, may approach 100% by weight of the indicator and/or reactant solution and Is typically In the range of from about 25 to 75% by weight based on the weight of the respective solution.

In an important aspect of the present invention, the flow rate of the indicator or reactant throughout the tube is controlled by providing at least two material changes of direction as previously defined for the timing device when affixed to a substrate such as a product package. In a preferred form of the invention there will be at least two material changes of direction equal to or about 180°.

As specifically shown in FIG. 1, the flow of the Indicator or reactant from the reservoir 10*a* undergoes a first material change of direction from point (x) to point (y) and a second material change of direction from point (y) to point (z). The change of direction from point (x) to point (y) is about 180' as is the change in direction from point (y) to point (z). In the embodiment of FIG. 1, the timing device provides for leg portions 4*a* and 4*b* to extend upwardly to the same elevation. In other embodiments of the invention, the respective leg portions extend upwardly to different elevations (e.g. leg portion 4*a* may extend upwardly to an elevation exceeding the elevation of leg portion 4*b*).

Figure 2:
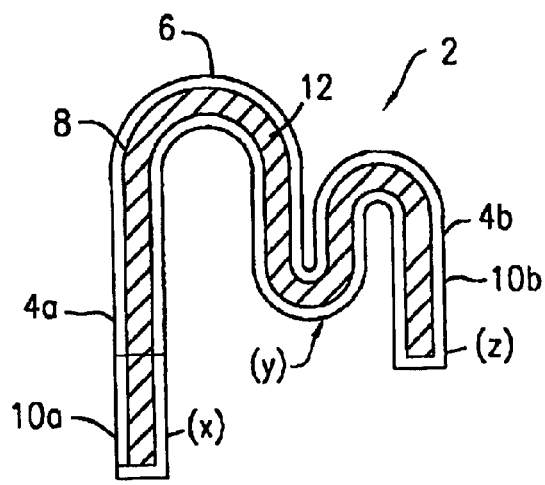
FIG. 2 is a front elevational view of a second embodiment of the timing device of the present invention.
Figure 3:
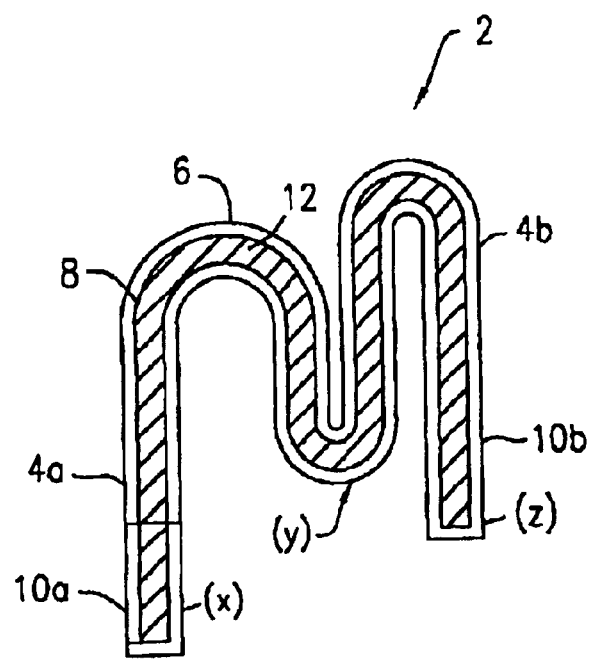
FIG. 3 is a front elevational view of a third embodiment of the timing device of the present invention.

Referring to FIGS. 2 and 3, the respective timing devices 2 have one leg portion which extends above the other leg portion. In particular, FIG. 2 shows a timing device in which the leg portion 4*a* extends above the leg portion 4*b* while in the embodiment of FIG. 3, the leg portion 4*b* extends above the leg portion 4*a*. In each embodiment the tube is shaped so that the indicator or reactant must travel through three material changes of direction before reaching the opposed end of the tube.

The embodiments of FIGS. 2 and 3 will generally provide a shorter measurable period of time than the embodiment of FIG. 1 because the total length of the respective tubes is shorter than the length of the tube in the embodiment of FIG. 1. Thus, the length of the tube may be a factor in customizing a timing device with a desirable measurable period of time for a particular application.

Figure 4:
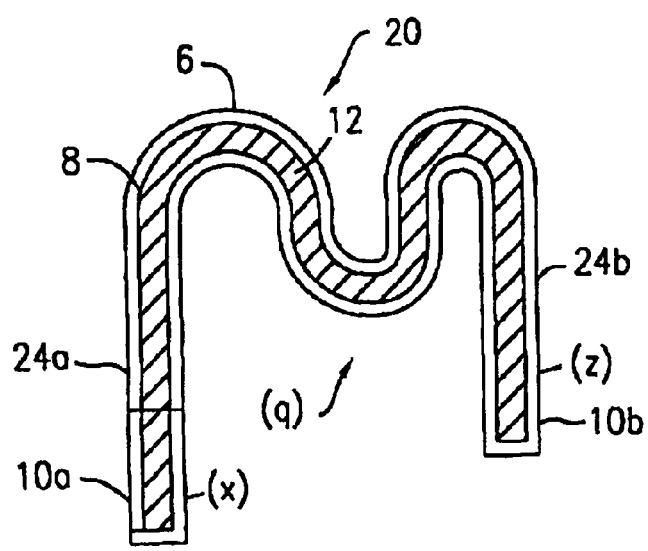
FIG. 4 is a front elevational view of a fourth embodiment of the timing device of the present invention.

As previously indicated, the timing device of the present invention employs at least two material changes of direction in the pathway for the flow of an indicator or reactant. In the embodiments of FIGS. 1–3, each material change of direction is about 180°. In the embodiment shown in FIG. 4, one of the material changes of direction is less than 180°. Referring to FIG. 4, the timing device 2 provides a tube 20 with respective leg portions 24*a* and 24*b*, curvilinear central section 26, and respective reservoirs 30*a* and 30*b* defining a pathway 28 for the flow of the indicator and/or reactant. The tube 20 has a first material change of direction from point (x) to point (q) of less than 180°. In this embodiment, the change from point (x) to point (q) is about 135° and results in generally a shorter measurable period of time then the measurable period of time resulting from about a 180' change in direction as used exclusively in the embodiments of FIGS. 1-3. Thus, the angle of each material change of direction may be a factor in customizing a timing device with a desirable measurable period of time for a particular application.

Figure 5:
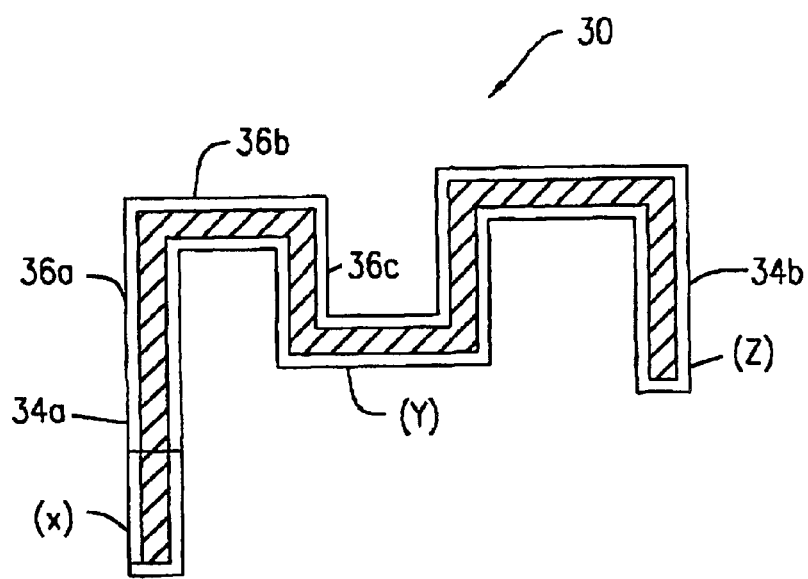
FIG. 5 is a front elevational view of a fifth embodiment of the timing device of the present invention.

In the embodiments of FIGS. 1–4, the tube is curvilinear as evidenced by reference numeral 6 at the position where the pathway defined by the tube undergoes a material change of direction. As shown in the embodiment of FIG. 5, the leg portions need not be curvilinear and may assume a more angled shape. In particular, FIG. 5 shows a timing device 30 having a leg portion 34a which changes direction in a series of 90° angles so that each segment 36 of the tube is perpendicular to an adjacent tube segment. For example, tube segment 36a is perpendicular to tube segment 36b which is perpendicular to tube segment 36c, etc. The embodiment of FIG. 5 provides a pathway that undergoes two material changes of direction of about 180° C. from point (x) to point (y) and from point (y) to point (z) as with the embodiment of FIGS. 1–3, but generally provides a longer measurable period of time than the previous embodiments. Thus, the employment of straight or curvilinear pathways may be a factor in customizing a timing device with a desirable measurable period of time for a particular application.

Figure 6:
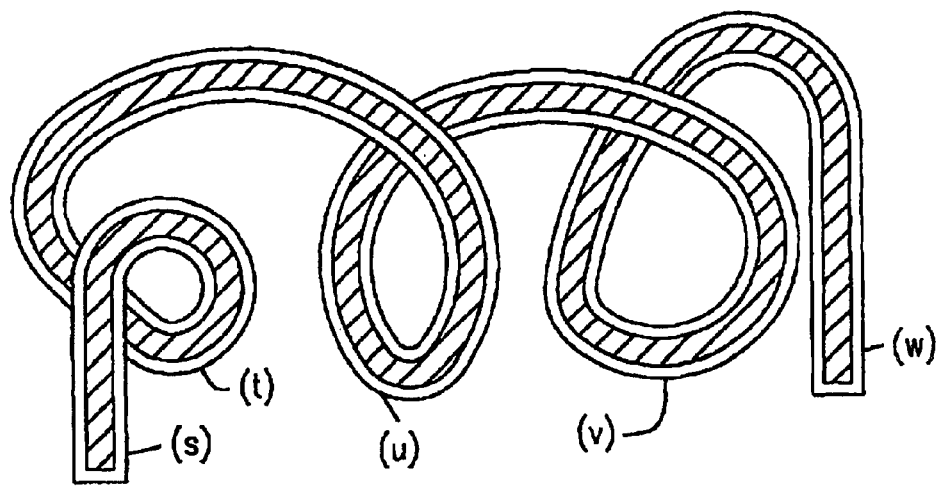
FIG. 6 is a front elevational view of a sixth embodiment of the timing device of the present invention.

More than two material changes of directions may be used to increase the measurable period of time. By way of example, an embodiment showing four material changes of direction in the form of coils is shown in FIG. 6 between consecutive points (s), (t), (u), (v) and (w). It will be appreciated that the number of material of material changes of direction can be increased by increasing the number of coils within the timing device.

Figure 7:
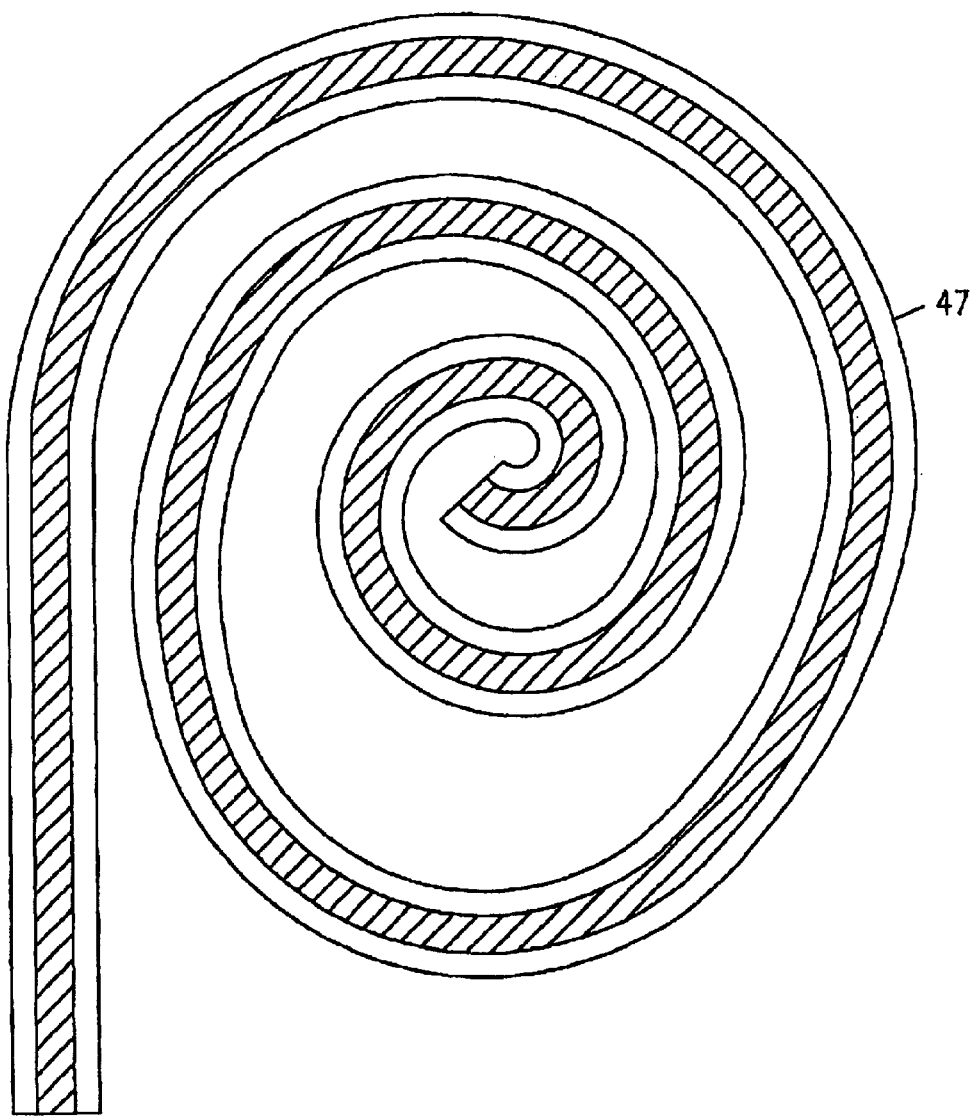
FIG. 7 is a front elevational view of a seventh embodiment of the timing device of the present invention.

In a further embodiment of the invention as shown in FIG. 7, a circular pathway comprised of a plurality concentric loops 47 for the timing device may be employed with each looped circuit amounting to two material changes of direction (two 180° changes of direction).

In each of the embodiments of the invention, previously described, the reactant contained within a reservoir (e.g. 10a) travels the entire length of the wick until it reaches the reservoir (e.g. 10b) containing the indicator at which time a color change occurs. The time it takes for the reactant to travel through the wick and into the reservoir 10b containing the indicator corresponds to the desired shelf life of the product and when the color change occurs the user knows that the product should be discarded or rejuvenated. In special "window" embodiments, the period of time and the initial reaction time are not the same; rather the desired period of time is for a color change to occur at a particular location along the tube.

In another embodiment of the invention both the reactant contained in the reservoir 10a and the indicator contained in the reservoir 10b travel through the wicking material and eventually contact each other at some point within the passageway 8 of the device 2. By suitably selecting reactants and indicators as well as the type and density of the wicking material, and optionally a viscosity modifying agent, the point of contact of the reagent and indicator and their time of travel can be accurately predicted and controlled.

The embodiments of the present invention as described provide for the movement of the reactant alone or the movement of both the reactant and the indicator through the wicking material and eventual contact causing a visible color change. It will be understood that in accordance with the present invention, the reactant may remain within the reservoir 10a while the indicator moves from the reservoir 10b through the wicking material over the entire length of the passageway 8 into the reservoir 10a where a reaction occurs causing a color change. In all of these embodiments the occurrence of a color change coincides with the useful shelf life of the product. When the color change occurs, the product is discarded or rejuvenated.

However, the present invention is applicable to the employment of a color change as a continuous indication of the passage of time so that the user can readily identify how much time has passed since the product has been used and how much time remains until the product must be discarded. In this embodiment of the invention, it is desirable to place either the reactant or the indicator throughout the wicking material and let the other of the reactant and indicator be absorbed through the wicking material from one of the reservoirs causing a continuous color change from one reservoir to the other.

For example, if a product has a useful shelf life of approximately five weeks, the timing device of the present invention may be marked with weeks 1–5 (i.e. wk1=the first week; wk2=the second week, etc). Thus, as the color change commences from the beginning of use of the product and passes to the marker indicating week one (wk1) the user will know that one week has passed since the product was used and about four weeks remain before the product must be discarded. It will be understood that the timing device can be constructed so that longer or shorter periods of time may be indicated depending on the type of reactant and indicator, the type and density of the wicking material, and the optional use of a viscosity modifying agent.

The timing device of the present invention can be contained within a package or housing which has one or more ports or windows that enables the user to view the device to observe a color change at one or more locations.

Figure 8:
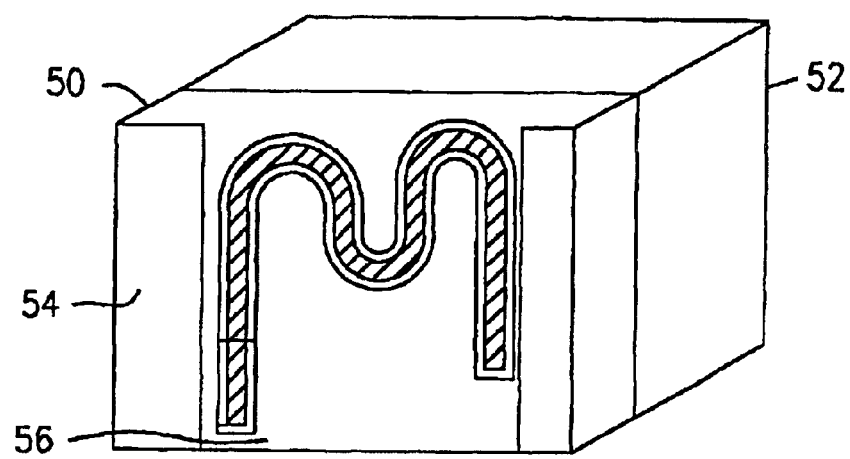
FIG. 8 is a perspective view of the timing device of FIG. 1 contained within a product package with the entire timing device visible.
Figure 9:
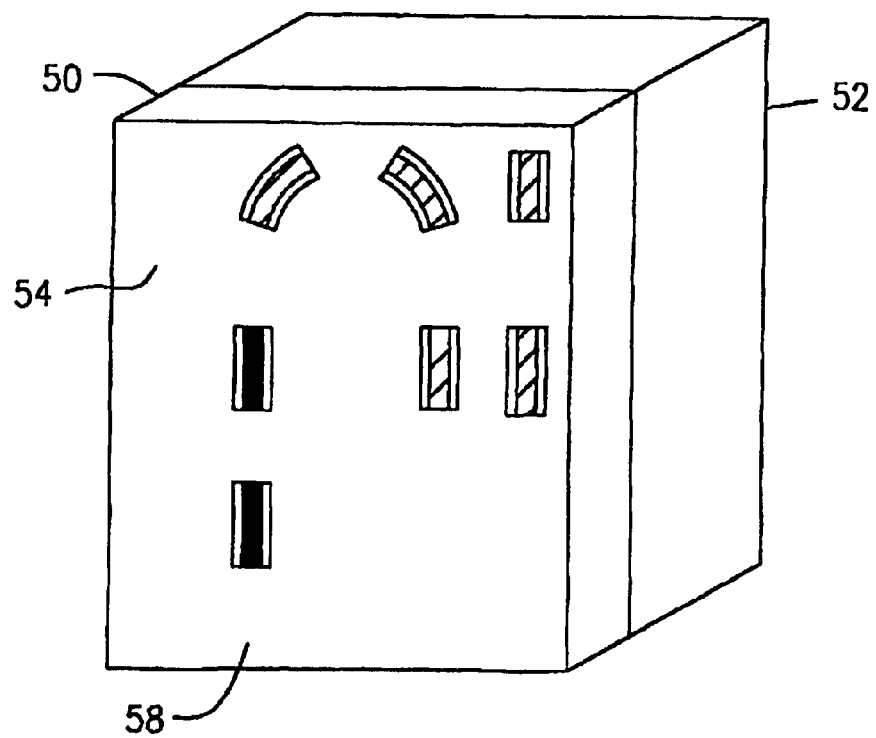
FIG. 9 is a perspective view of the timing device of FIG. 1 contained within a product package with spaced apart portions of the timing device visible.

Referring to FIGS. 8 and 9, there is shown an embodiment of the timing device shown in FIG. 1 contained within a housing 50 of a package 52 which contains a consumer product. The housing 50 provides sufficient space to house the timing device 2. The housing 50 has a front face 54 with a clear window 56 enabling the viewer to view the entire timing device as specifically shown in FIG. 8. In this embodiment of the invention, the user can view the entire timing device as discussed above in connection with FIGS. 1–7. Thus, all color changes and the location of all color changes can be observed by the user.

In another embodiment of the invention as shown in FIG. 9, the package 52 may be provided with a housing 50 in which the front face 54 contains one or more ports or windows 58 which shows periodic color changes through the window indicating the passage of a fixed period of time such as one week or one month. If only one window is used, it should be at the point that there is a final color change indicating that the product needs to be replaced or rejuvenated. The employment of multiple windows 58 enables the user to periodically observe how much time has passed and how much time remains of the product shelf life. In the specific embodiment of FIG. 9, there are seven windows with the first two windows indicating a color change. If each window was indicative of the passage of one week of time, then the product would have been used for two weeks with about four weeks remaining of the product shelf life.

The timing device of the present invention can be affixed to a product by adhesive or the like or can be prepackaged with the product as indicated in the embodiments of FIGS. 8 and 9. In some cases, it is desirable to package the reactant and indicators in the respective reservoirs within a breakable container which can be broken by pressure applied to the user. Such containers include capsules made of a variety of materials including gelatins and the like. The breakable capsules enable the user to commence the start of the product life and thereby disregard the period of time from manufacture to purchase by the user.

The wicking material employed in the timing device of the present invention may be arranged in a uniform profile or a non-uniform profile. The term "uniform profile" shall mean that the cross-sectional area and shape of the wicking material is the same throughout the length thereof. The term "non-uniform profile" shall mean that the cross-sectional area and shape of the wicking material is not the same throughout the length thereof.

As previously indicated the timing device may employ a reactant or indicator which is comprised of a solid material. The reservoir 10b may contain a solid indicator (e.g. cobalt chloride) while a reservoir 10a contains a liquid reactant (e.g. water). Water travels from the reservoir 10a to the reservoir 10b to cause a color change (e.g. from blue to pink) which is observable through the window 26.

The time for a color change to occur will in part be dependent on the time it takes the reactant (e.g. water) to reach the solid indicator (e.g. cobalt chloride). It will be observed that contact of the liquid reactant and solid indicator will result in the formation of a solution in the reservoir 10b. Due to capillary action, and concentration gradients, the solution (which will have a pink color in the example mentioned above) will migrate toward the reservoir 10a. As a consequence, it is possible to place a window along the path of the wicking material to observe the "pink" colored solution. Thus the length of the period of time can be extended because the liquid indicator must first travel from reservoir 10b to 10a to cause a color change therein and then for an additional period of time until the colored solution in the reservoir 10a reaches the window where it is observed by the consumer. Alternatively, the solid indicator may be placed in reservoir 10b and liquid reactant may be placed in reservoir 10a.

EXAMPLE 1

A timing device of the type shown in FIG. 1 was constructed by inserting into the tube grade 3 chromatographic paper obtained from Whatman, Inc. of Clifton, N.J. as the wicking material. Reservoirs were made from the bulbs of 0.5 ml disposable pipettes obtained from Samco Scientific Incorporated of San Fernando, Calif.

A reactant solution was prepared by combining 7.35 weight % of deionized water, 66.18 weight % of glycerin, 24.51 weight % of propylene glycol and 1.96 weight % of glacial acetic acid. An indicator solution was prepared by combining 7.50 weight % of deionized water, 67.47 weight % of glycerin, 24.98 weight % of propylene glycol and 0.05 weight % of litmus. The reactant solution was clear while the indicator solution was blue.

In order to activate the timing mechanism, 0.6 ml of the indicator solution was placed in the indicator reservoir and 0.6 ml of the acidic solution was placed in the reactant reservoir. The wick was then placed in the reservoirs until each end of the wick touched the bottom of the reservoirs. The entire assembly was then wrapped in a covering of plastic film.

The timer duration was noted as the time it took the indicator reservoir to turn from blue to red. Multiple samples were tested in this matter at 40° F. in a refrigerator or in a thermostatic chamber which maintained a constant temperature of 80° F. and a relative humidity of 80%. The results are shown in Table 1.

TABLE 1

| Samples | Duration (Room Temp.) |
| --- | --- |
| FIG. 2 | 28 ± 4 days |
| FIG. 3 | 34 ± 4 days |

Both embodiments of FIGS. 2 and 3 provided significantly longer measurable periods of time than that obtained using an inverted U-shaped tube of the same height and tube diameter.

What is claimed is:

1. A timing device for determining the passage of a preselected period of time comprising:
   (a) a tube having opposed ends with one of the opposed ends extending downwardly below the level of the remaining portion of the tube, one of said opposed ends having a first reservoir for storing a reactant or an indicator, the other of said reactant or indicator being stored in the tube but not in the, first reservoir, said tube undergoing at least two material changes in direction from one of the opposed ends to the other;
   (b) transport means extending from the reservoir to the other of the opposed ends of the tube for transporting at least one of the reactant or the indicator until they contact each other;
   (c) said reactant; and
   (d) said indicator which when in contact with the reactant via the transport means emits an observable change in a property wherein the minimum length of the period of time corresponds to the time it takes for the reactant and indicator to contact each other.

2. The timing device of claim 1 wherein the other of said opposed ends has a second reservoir.

3. The timing device of claim 2 wherein the reactant is initially present in the first reservoir at one of said ends and the indicator is present in the second reservoir at the other of said ends.

4. The timing device of claim 1 wherein at least one of said reactant and said indicator is a liquid.

5. The timing device of claim 4 wherein each of said reactant and indicator is a liquid.

6. The timing device of claim 5 wherein the reactant is selected from the group consisting of an acid and a base.

7. The timing device of claim 6 wherein the indicator changes color when contact by the reactant.

8. The timing device of claim 1 wherein the indicator comprises a color changing compound and a viscosity modifying agent.

9. The timing device of claim 8 wherein the viscosity modifying agent is selected from the group consisting of water, glycerine, alkylene glycols and mixtures thereof.

10. The timing device of claim 8 wherein the reactant further comprises a viscosity modifying agent.

11. The timing device of claim 1 wherein the transport means is comprised of porous material.

12. The timing device of claim 1 wherein the transport means is comprised of a wicking material.

13. The timing device of claim 12, wherein the wicking material is selected from the group consisting of woven fabrics, non-woven fabrics and combinations thereof.

14. The timing device of claim 12, wherein the wicking material is selected from the group consisting of polyesters, polyacrylates, polyacrylamides, polypropylene and copolymers thereof, natural or synthetic cellulosic materials, wood, paper, cellulosic polymers, cotton, wool, fiberglass, silica gel, ceramics and combinations thereof.

15. The timing of device of claim 14 wherein at least one of the reactant and indicator are present in the wicking material.

16. The timing device of claim 12 wherein the reactant and indicator contact each other to produce a liquid exhibiting a change of property, said period of time including the length of time it takes the liquid to travel a predetermined distance through the wicking material.

17. The timing device of claim 1 wherein the indicator is an anhydrous compound and the reactant is water.

18. The timing device of claim 1 wherein the tube further comprises a scavenger material.

19. The timing device of claim 18 wherein the reactant reacts with the scavenger material preferentially to prevent substantial reaction of the reactant with the indicator until the scavenger material is substantially consumed.

20. The timing device of claim 1 further comprising an intermediary substance wherein the reactant reacts with the intermediary substance to produce a second reactant which reacts with the indicator to produce said observable change of property.

21. The timing device of claim 1 wherein the reactant or indicator is a solid material.

22. The timing device of claim 21 wherein the other of said reactant or indicator travels via the transport means to the solid material.

23. The timing device of claim 1 comprising a first pair of leg portions defining a first material change of direction and a second pair of leg portions defining a second material change in direction.

24. The timing device of claim 23 wherein the highest point of the first pair of leg portions is the same as the highest point of the second pair of leg portions.

25. The timing device of claim 23 wherein the highest point of the first pair of leg portions is different than the highest point of the second pair of leg portions.

26. The timing device of claim 25 wherein the highest point of the first pair of leg portions is greater than the highest point of the second pair of leg portions.

27. The timing device of claim 25 wherein the highest point of the first pair of leg portions is less than the highest point of the second pair of leg portions.

28. The timing device of claim 23 wherein the leg portions of the first pair of leg portions are perpendicular to each other.

29. The timing of claim 1 wherein the tube comprises at least three material changes of direction.

30. The timing device of claim 1 wherein at least one material change of direction is equal to or about 180°.

31. The timing device of claim 30 wherein each material change of direction is equal to or about 180°.

32. A package having on an outer surface thereof a timing device of claim 1.

33. The package of claim 32 comprising a first pair of leg portions defining a first material change of direction and a second pair of leg portions defining a second material change in direction.

34. The package of claim 33 wherein the highest point of the first pair of leg portions is the same as the highest point of the second pair of leg portions.

35. The package of claim 33 wherein the highest point of the first pair of leg portions is different than the highest point of the second pair of leg portions.

36. The package of claim 35 wherein the highest point of the first pair of leg portions is greater than the highest point of the second pair of leg portions.

37. The package of claim 35 wherein the highest point of the first pair of leg portions is less than the highest point of the second pair of leg portions.

38. The package of claim 33 wherein each leg portion of the first pair of leg portion is perpendicular to the other leg portion.

39. The package of claim 32 wherein said tube comprises at least three material changes of direction.

40. The package of claim 32 wherein at least one material change of direction is equal to or about 180°.

41. The package of claim 40 wherein each material change of direction is equal to or about 180°.

42. A method of determining the passage of a preselected period of time corresponding to the useful life of a product comprising:

attaching to said product or to a package containing said product a timing device of claim 1.

43. The method of claim 42 comprising controlling the rate of flow of at least one of the reactant and indicator through the transport means.

44. The method of claim 42 wherein the reactant and indicator are contained within separate breakable containers, said process further comprising breaking said containers to commence the preselected period of time.

* * * * *